United States Patent
Melkent (10) Patent No.: US 8,187,328 B2
(45) Date of Patent: May 29, 2012

(54) EXPANDABLE CONTAINMENT DEVICES AND METHODS

(75) Inventor: Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1430 days.

(21) Appl. No.: 11/650,747

(22) Filed: Jan. 8, 2007

(65) Prior Publication Data

US 2008/0167726 A1 Jul. 10, 2008

(51) Int. Cl.
*A61F 2/44* (2006.01)
(52) U.S. Cl. .................................................... 623/17.11
(58) Field of Classification Search ..... 623/17.11–17.16
See application file for complete search history.

(56) References Cited

U.S. PATENT DOCUMENTS

| | | | |
|---|---|---|---|
| 5,236,460 A | 8/1993 | Barber | |
| 5,480,442 A | 1/1996 | Bertagnoli | |
| 6,344,057 B1 | 2/2002 | Rabbe et al. | |
| 6,616,695 B1 | 9/2003 | Crozet et al. | |
| 6,641,587 B2 * | 11/2003 | Scribner et al. | 606/93 |
| 6,709,458 B2 * | 3/2004 | Michelson | 623/17.15 |
| 6,908,485 B2 | 6/2005 | Crozet et al. | |
| 7,235,102 B2 * | 6/2007 | Ferree et al. | 623/17.12 |
| 2003/0195628 A1 * | 10/2003 | Bao et al. | 623/17.12 |
| 2004/0186569 A1 | 9/2004 | Berry | |
| 2005/0137707 A1 * | 6/2005 | Malek | 623/17.12 |
| 2005/0209595 A1 * | 9/2005 | Karmon | 606/76 |
| 2008/0058930 A1 * | 3/2008 | Edie et al. | 623/17.11 |
| 2008/0058931 A1 * | 3/2008 | White et al. | 623/17.11 |
| 2008/0183210 A1 * | 7/2008 | Zucherman et al. | 606/246 |

* cited by examiner

*Primary Examiner* — Eduardo C Robert
*Assistant Examiner* — Summer Kostelnik (57) ABSTRACT

An expandable containment device is provided for use in containing a flowable material. The containment device includes an expandable housing extending along a longitudinal axis and defining an interior region, and including a first housing portion movably engaged with a second housing portion to allow expansion of the housing generally along the longitudinal axis to provide the housing with an axial dimension extending between adjacent bone structures. The containment device further includes an input port in fluid communication with the interior region of the housing and configured to deliver a flowable material into the interior region of the housing.

14 Claims, 6 Drawing Sheets

EXPANDABLE CONTAINMENT DEVICES AND METHODS

TECHNICAL FIELD

The present invention relates generally to the field of surgical devices and methods, and more particularly relates to expandable containment devices and methods.

BACKGROUND

It is sometimes necessary to remove one or more vertebrae, or a portion of the vertebrae, from the human spine in response to various pathologies. For example, one or more of the vertebrae may become damaged as a result of tumor growth, or may become damaged by trauma or other events. Excision of at least a portion of the vertebral body is typically referred to as a corpectomy or vertebrectomy procedure. An implant may be placed within the intervertebral space between the remaining vertebrae to provide structural support and stability to the spine. In some instances, the implant inserted between the vertebrae is designed to facilitate fusion between the remaining vertebrae. In other instances, the implant is designed to replace the function of the excised vertebral body and discs.

Many implants are known in the art for use in association with a corpectomy procedure. One class of implants is configured to directly replace the removed vertebra or vertebrae. Another class of implants is configured for insertion into the intervertebral space in a collapsed state and then expanded once properly positioned within the intervertebral space between the remaining adjacent vertebrae. The use of expandable implants may be advantageous since a smaller incision is required to insert the implant into the intervertebral space. Additionally, expandable implants may assist with restoring proper loading to the spinal anatomy and achieving more secure fixation of the implant. Implants which include insertion and expansion members that have a narrow profile may also provide clinical advantages.

In some instances, the cavity or void left when a vertebral body or portion of a vertebral body is removed is filled with a bone graft and/or bone cement or paste to provide support and stability to the spinal column. Osteosynthesis instrumentation is sometimes used to prevent relative movement between the adjacent unaffected vertebrae. However, most of these devices are relatively expensive to manufacture and can be difficult to use.

There remains a need for improved surgical devices and methods for use in the replacement of one or more vertebral bodies or other orthopedic structures.

SUMMARY

The present relates generally to the field of surgical devices and methods, and more particularly relates to expandable containment devices and methods. While the actual nature of the invention covered herein can only be determined with reference to the claims appended hereto, certain forms of the invention that are characteristic of the preferred embodiments disclosed herein are described briefly as follows.

In one form of the present invention, an expandable containment device is provided for use in containing a flowable material. The containment device includes an expandable housing extending along a longitudinal axis and defining an interior region, and including a first housing portion movably engaged with a second housing portion to allow expansion of the housing generally along the longitudinal axis to provide the housing with an axial dimension extending between adjacent bone structures. The containment device further includes an input port in fluid communication with the interior region of the housing and configured to deliver a flowable material into the interior region of the housing.

In another form of the present invention, an expandable containment device is provided for use in containing a flowable material. The containment device includes an expandable housing extending along a longitudinal axis and defining an interior region. The expandable housing includes first and second housing portions, each defining a hollow interior, with the hollow interiors cooperating with one another to define the interior region of the housing. One of the housing portions is telescopically received within the hollow interior of the other housing portion to allow expansion of the housing generally along the longitudinal axis to provide the housing with an axial dimension extending between adjacent bone structures. The containment device further includes an input port in fluid communication with the interior region of the housing and configured to deliver a flowable material into the interior region of the housing.

In another form of the present invention, a method is provided for supporting adjacent bone structures, including providing an expandable containment device, positioning the expandable containment device within a space between the adjacent bone structures, delivering a flowable material into the expandable containment device, and expanding the expandable containment device to extend between the adjacent bone structures.

It is one object of the present invention to provide improved containment devices and methods. Further objects, features, advantages, benefits, and aspects of the present invention will become apparent from the drawings and description contained herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
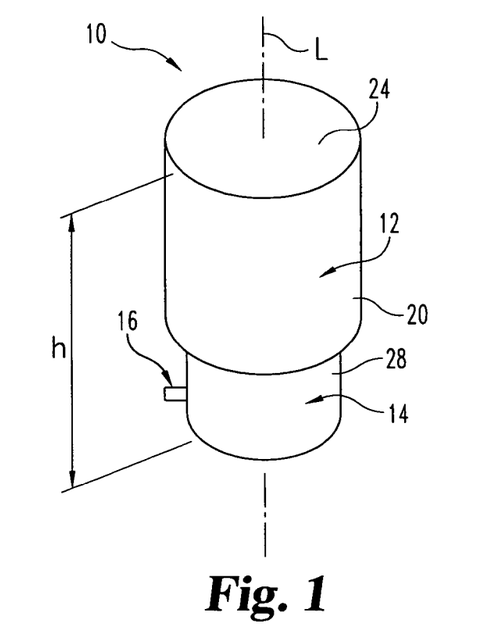
FIG. 1 is a perspective view of an expandable containment device according to one form of the present invention.
Figure 2:
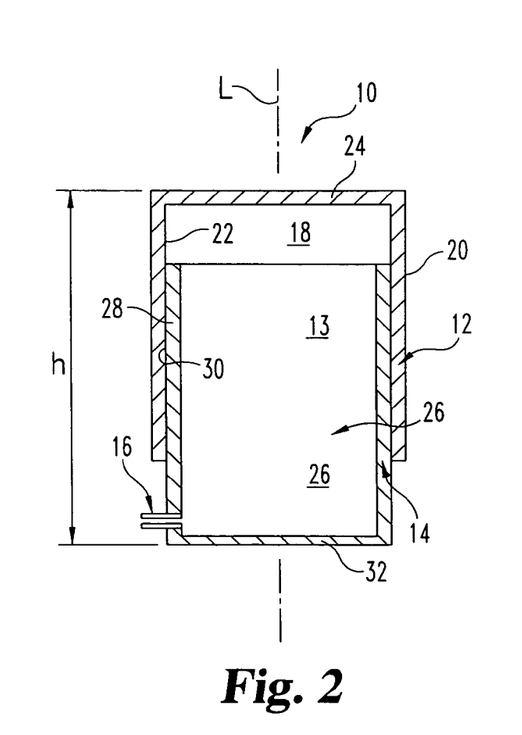
FIG. 2 is a cross-sectional view of the expandable containment device of FIG. 1.

Referring collectively to FIGS. 1 and 2, shown therein is an expandable containment device 10 according to one form of the present invention. The containment device 10 is used to contain a flowable material which preferably cures or sets to a non-flowable or hardened state to form a support column or strut to maintain a fixed spacing between two vertebrae of the spine following removal of at least a portion of an intermediate vertebra and the adjacent disc material. In one embodiment of the invention, the containment device 10 is used in association with the lumbar region of the spine. However, it is also contemplated that the containment device 10 may be used in association with other regions of the spine, including the cervical and thoracic regions. It is further contemplated that the containment device 10 may be used in association with other bone structures outside of the spine.

In the illustrated embodiment of the invention, the expandable containment device 10 extends generally along a longitudinal axis L and includes an upper housing 12, a lower housing 14 and an input port 16. In one embodiment, the upper and lower housings 12, 14 each have a generally cylindrical configuration. However, as will be discussed below, other shapes and configurations are also contemplated. In the illustrated embodiment, the lower housing 14 is sized and configured to be telescopically received within a hollow interior or axial passage 18 defined by the upper housing 12. However, in other embodiments, the upper housing 12 may be sized and configured to be telescopically received within a hollow interior or axial passage defined by the lower housing 14. Prior to or during injection or delivery of the flowable material into the containment device 10, the relative positions of the upper and lower housings 12, 14 are telescopically adjusted generally along the longitudinal axis L, thereby allowing the overall height h or axial length of the containment device 10 to be adjusted to a select height or axial length.

In the illustrated embodiment of the invention, the upper housing 12 has a generally cylindrical or tubular configuration defining a hollow interior 18 bound by an axial side wall 20 defining an inner surface 22 and an end wall 24. Similarly, the lower housing 14 has a generally cylindrical or tubular configuration defining a hollow interior 26 bound by an axial side wall 28 defining an outer surface 30 and an end wall 32. As indicated above, in the illustrated embodiment, the lower housing 14 is sized and configured to be telescopically received within the hollow interior or axial passage 18 defined by the upper housing 12, thereby allowing the overall height h or axial length of the containment device 10 to be adjusted to a select height or axial length.

In one embodiment of the containment device 10, the inner surface 22 of the upper housing 12 is sized and shaped to correspond with the outer surface 30 of the lower housing 14 to allow for telescopic movement of the upper housing 12 relative to the lower housing 14 along the longitudinal axis L. In the illustrated embodiment, the inner surface 22 of the upper housing 12 and the outer surface 30 of the lower housing 14 are substantially smooth and devoid of any surface projections (e.g., threads) to facilitate relatively uninhibited telescopic movement of the upper housing 12 relative to the lower housing 14. In this manner, the containment device 10 is configured to allow for infinite adjustment to the overall height h of the containment device 10. Accordingly, the overall height h of the expandable containment device 10 can be precisely adjusted to fit between respective vertebrae.

As illustrated in FIG. 2, the upper and lower housings 12, 14 are configured and cooperate with one another to provide a substantially enclosed interior region 13 for containing the flowable material that is injected or delivered into the containment device 10. In the illustrated embodiment of the invention, each of the upper and lower housings 12 and 14 is provided with a tubular configuration defining a hollow interior or axial passage 18, 26, respectively. However, in other embodiments, only the upper housing 12 is provided with a tubular configuration defining a hollow interior or axial passage 18, with the lower housing 14 having a substantially solid configuration. In this embodiment, the volume of the inner region of the containment device to be filled with a flowable material is reduced. An inverse embodiment is likewise contemplated, wherein only the lower housing 14 is provided with a tubular configuration defining a hollow interior or axial passage 26, with the upper housing 12 having a substantially solid configuration.

The end wall 24 of the upper housing 12 and the end wall 32 of the lower housing 14 are positioned for engagement with the adjacent vertebral body or bone. In the illustrated embodiment, the end walls 24 and 32 are formed integral with the upper and lower housings 12 and 14, respectively. However, in other embodiments, the end walls 24 and 32 may be formed separately and attached to the housings via any attachment technique know to those of skill in the art. In the illustrated embodiment, the end walls 24 and 32 have a substantially smooth outer engagement surface. Additionally, in other embodiments, the outer engagement surface of the end walls 24 and 32 may be provided with various types of anchor elements to facilitate gripping of the adjacent vertebral body or bone to inhibit movement of the containment device 10 once positioned within the intervertebral space.

In the illustrated embodiment of the containment device 10, the end walls 24 and 32 have a solid or non-perforated configuration, and do not define any openings or apertures extending therethrough. However, in other embodiments, either or both of the end walls 24 and 32 may be provided with one or more openings or apertures extending through the outer engagement surfaces and in communication with the interior region 13 of the containment device. Additionally, although the axial side walls 20 and 28 of the upper and lower housings 12 and 14 are illustrated as having a solid or non-perforated configuration, in other embodiments, either or both of the axial side walls 20 and 28 may be provided with one or more openings or apertures extending therethrough and in communication with the interior region 13 of the containment device. As should be appreciated, providing the side walls and/or the end walls with openings or apertures in communication with the interior region 13 of the containment device 10 may facilitate vascularization or bone growth into or onto the material injected or delivered into the containment device once set or cured to a hardened state.

As illustrated in FIG. 2, the input port 16 of the containment device 10 is positioned in fluid communication with the interior region 13 of the containment device 10. The input port 16 is configured for connection with a material injector or delivery device or system to allow for the injection or delivery of a flowable material into the interior region 13 of the containment device 10. Although the input port 16 is illustrated as an external feature, it could also be provided as an internal feature as well (e.g., a threaded opening, lure-lock, etc.). Additionally, although the input port 16 is illustrated as being associated with the lower housing 14, it should be understood that the input port 16 may alternatively be associated with the upper housing 12.

As indicated above, the material which is injected or delivered into the containment device 10 is a flowable material which preferably cures or sets to a non-flowable or hardened state to form a support column or strut to maintain a fixed space between two vertebral bodies. In one embodiment of the invention, the flowable material comprises a bone cement or paste such as, for example, polymethylmethacrylate (PMMA). PMMA is typically made from methylmethacrylate, polymethylmethacrylate, esters of methacrylic acid, or copolymers containing polymethylmethacrylate and polystyrene. However, it should be understood that other types of bone cement or paste, or other hardenable or curable materials, are also contemplated as falling within the scope of the present invention. For example, and without limitation, the flowable material may comprise a semi-rigid flowable or hardenable material such as silicone or various types of urethane materials. It should further be understood that other types of flowable materials which are not necessarily hardenable or curable may be used is association with the present invention. For example, the flowable material may comprise beads or small particles or grains of material that may be injected or delivered into the containment device 10. Additionally, the flowable material may include bone growth promoting materials or substances such as bone graft material or bone morphogenic protein (BMP), therapeutic materials or substances, or any other biocompatible materials or substances that would occur to one of skill in the art. Additionally, the flowable material may be resorbable or non-resorbable.

Figure 3:
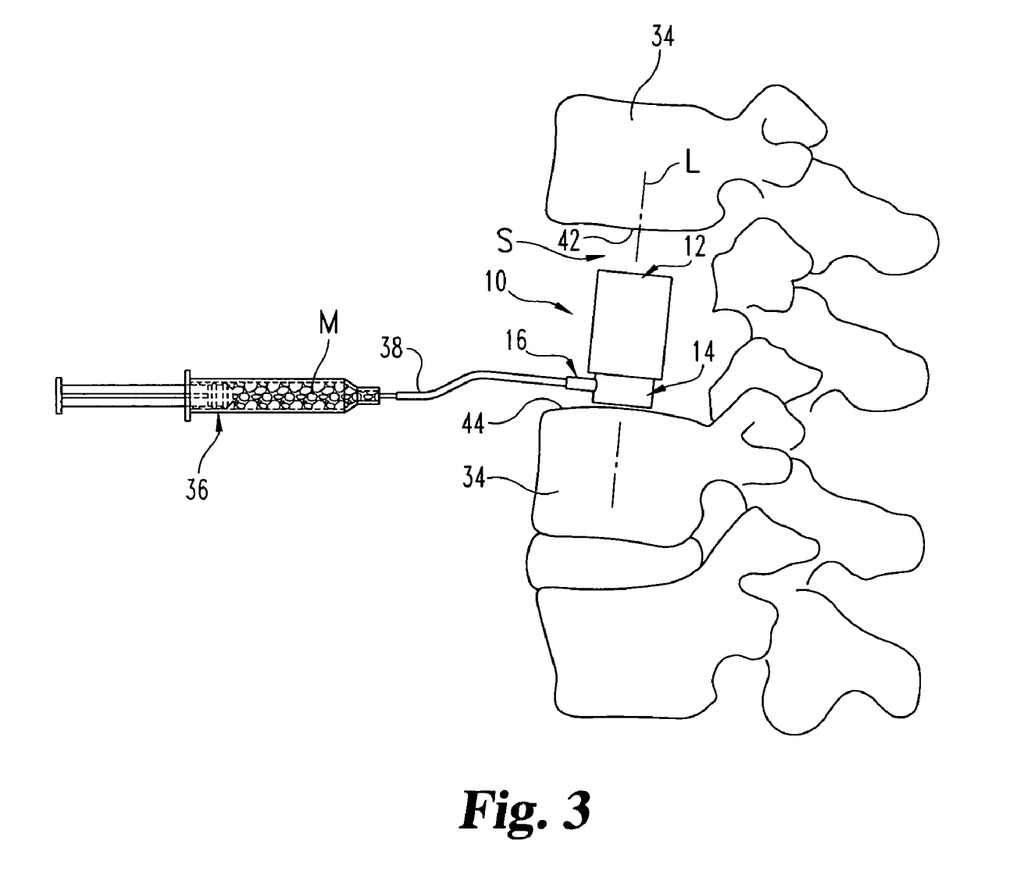
FIG. 3 illustrates the expandable containment device of FIG. 1, as positioned between adjacent vertebrae in a collapsed or contracted state.

Referring to FIG. 3, the containment device 10 is inserted into an intervertebral space S between two adjacent vertebrae 34 while in a contracted or collapsed state. Subsequent to insertion, a flowable material M is injected or delivered into the containment device 10. However, it is also contemplated that at least a portion of the flowable material M may be injected or delivered into the containment device 10 prior to insertion of the device 10 into the intervertebral space S. In the illustrated embodiment, an injector or delivery device 36 is connected or attached to the input port 16 via a delivery tube 38. However, in other embodiments, the delivery device 36 may be connected or attached directly to the input port 16. In the illustrated embodiment, the delivery device 36 comprises a hand held syringe-type device. However, other types of delivery devices or material delivery systems are also contemplated for use in association with the present invention.

Figure 4:
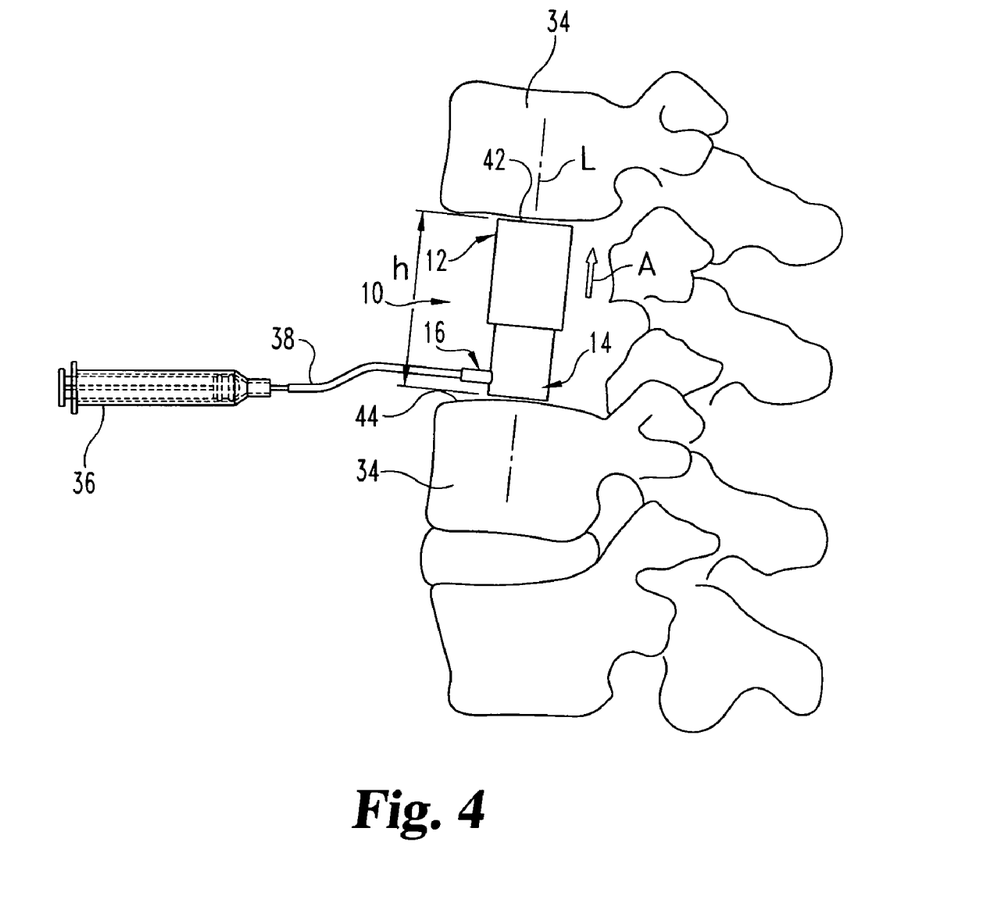
FIG. 4 illustrates the expandable containment device of FIG. 1, as positioned between adjacent vertebrae in an expanded state.

Referring to FIG. 4, once the containment device 10 is properly positioned within the intervertebral space S between the two adjacent vertebrae 34, the flowable material M is injected or delivered into the interior region 13 of the containment device 10 via activation of the delivery device 36. As the flowable material M is delivered into and fills the interior region 13 of the containment device 10, the upper and lower housings 12, 14 are axially displaced apart in a telescopic manner generally along the longitudinal axis L to expand the containment device 10 to an expanded state having a height h. When transitioned to the expanded state, the upper and lower end walls of the containment device 10 are engaged against the upper and lower vertebral surfaces 42 and 44. In the illustrated embodiment, the lower housing 14 is initially positioned proximately adjacent the lower vertebral surface 44 such that as the flowable material M fills the interior region 13, the upper housing 12 is axially displaced away from the lower housing 14 in the direction or arrow A to expand the containment device 10. However, other methods of expansion are also contemplated. Once transitioned to the expanded height h, the containment device 10 is maintained between the two adjacent vertebrae 32. The flowable material M is then allowed to set or cure to a harden state to provide a support column or strut extending between the adjacent vertebrae 34. Additional stabilization instrumentation or devices such as, for example, rods or plates may be anchored to the adjacent vertebrae 34 to provide additional support and stability to the spinal column to prevent or inhibit relative movement therebetween to facilitate fusion.

As should be appreciated, since the support column or strut formed by the hardened material bears most if not all of the loading exerted by the adjacent vertebral bodies or bone segments, the containment device 10, including the upper and lower housings 12 and 14, may be configured as a non-structural element(s) (i.e., non-load bearing structures) since the primary purpose of the containment device 10 is to contain the flowable material until set or cured to a hardened state. As a result, the materials used to form the containment device 10 do not have to be selected to withstand significant loading, but may instead be formed of materials that would not otherwise be used if the containment device 10 were exposed to significant loading such as, for example, plastic or polymeric materials. Additionally, since the containment device 10 is not exposed to significant loading, the thickness of the axial side walls and end walls of the upper and lower housings 12, 14 can be significantly reduced. As should be appreciated, forming the containment device 10 from a non-load bearing material having relatively thin wall thickness tends to reduce manufacturing and material costs, and also results in a light weight device that can be easily manipulated and inserted into the intervertebral space.

In one embodiment of the invention, delivery of the flowable material M into the interior region 13 of the containment device 10 generates internal fluid pressure which causes the upper and lower housings 12, 14 to expand apart in a telescopic manner to expand the containment device 10. However, in other embodiments of the invention, a distractor instrument (not shown) may be used to distract the upper and lower housings 12, 14 apart to the expanded state illustrated in FIG. 4 prior to or during injection or delivery of the flowable material M into the containment device 10. Additionally, in one embodiment of the invention, the adjacent vertebrae 34 are initially distracted apart via know distraction methods prior to insertion of the containment device 10 into the intervertebral space S. However, in other embodiments, expansion of the containment device 10 via delivery of the flowable material M into the interior region 13 and/or via a distractor instrument may be used to distract the adjacent vertebrae 34.

Figure 5:
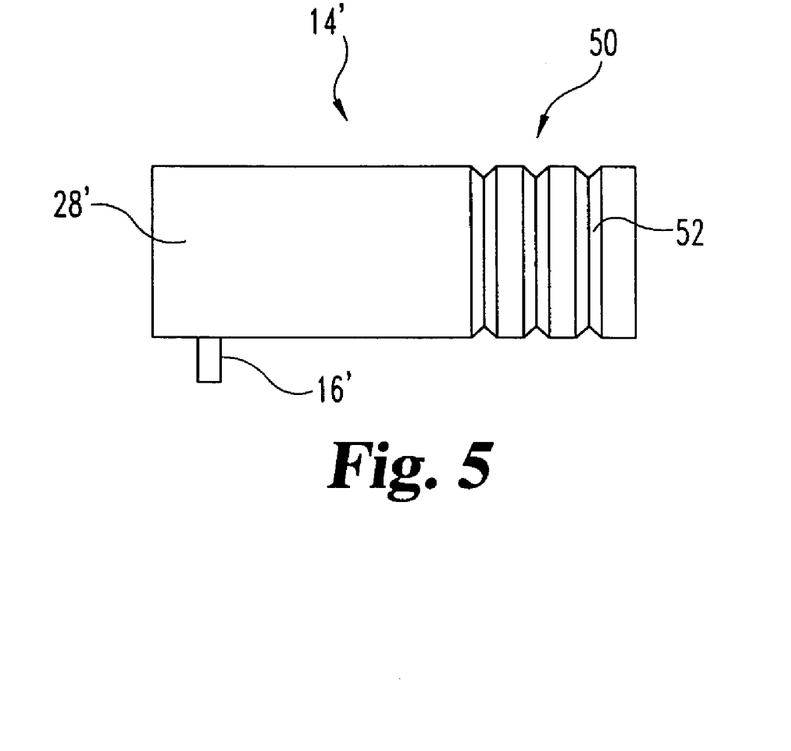
FIG. 5 illustrates a containment housing having a pre-scored section for use in association with an expandable containment device.

Referring to FIG. 5, shown therein is another embodiment of a housing 14' for use in association with the present invention. Similar to the housing 14 illustrated and described above, the housing 14' includes an axial side wall 28', and end wall (not show) and an input port 16'. However, the axial side wall 28' includes a pre-scored section 50 located adjacent an end portion of the housing 14'. The pre-scored section 50 includes a plurality of scores 52 that run peripherally about an outer surface of the axial side wall 28'. The scores 52 allow a portion of the axial side wall 28' to be quickly and easily broken off or trimmed away to shorten the axial dimension or height of the housing 14'. Specifically, the scores 52 allow for a predefined axial segment or section of the housing 14' to be quickly and easily broke off, trimmed away or otherwise removed from the open end of the housing 14'. Although not specifically illustrated, it should be understood that either or both of the upper and lower housings may be provided with a pre-scored section 50 to allow the axial dimension or height of either housing to be quickly and easily adjusted. As should be appreciated, providing the upper and lower housings with features that allow for a portion of the axial side wall to be quickly and easily broken off or trimmed away to shorten the axial dimension or height of the housing eliminates the need to provide housings of various sizes to provide the containment device with a select overall height or axial length. As a result, inventory levels may be significantly reduced.

Figure 6:
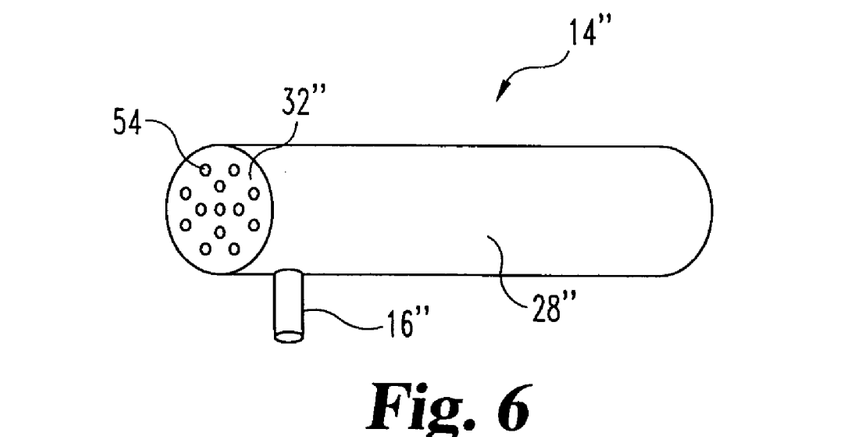
FIG. 6 illustrates a containment housing having an end wall with perforations for use in association with an expandable containment device.

Referring to FIG. 6, shown therein is another embodiment of a housing 14" for use in association with the present invention. Similar to the housing 14 illustrated and described above, the housing 14" includes an axial side wall 28", and end wall 32" and an input port 16". However, the end wall 32" defines a plurality of apertures or perforations 54 extending through the end wall 32" and in communication with the hollow interior of the housing 14". The apertures or perforations 54 allow for some of the flowable material M to exit the housings 14' to conform to the surface of the adjacent vertebral body or bone. Although the apertures or perforations 54 are illustrated as having a circular shape and a relative small size, other shapes, configurations and sizes are also contemplated as falling within the scope of the present invention. Additionally, it should also be understood that any number of apertures or perforations 54 may be provided, including a single aperture or perforation extending through the end wall 32". Although not specifically illustrated, it should be understood that either or both of the upper and lower housings may be provided with apertures or perforations 54 extending through the end wall and/or possibly the axial side wall.

Figure 7A:
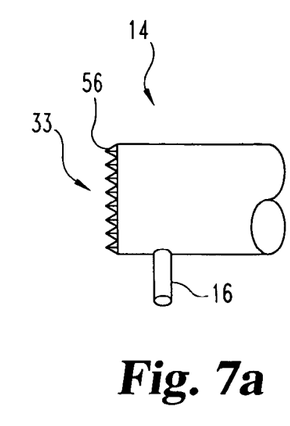
FIG. 7a illustrates an end portion of a containment housing having an end wall with spikes or teeth for use in association with an expandable containment device.
Figure 7B:
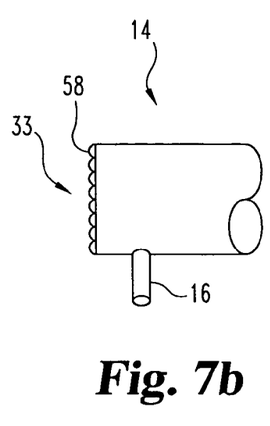
FIG. 7b illustrates an end portion of a containment housing having an end wall with projections or knurlings for use in association with an expandable containment device.
Figure 7C:
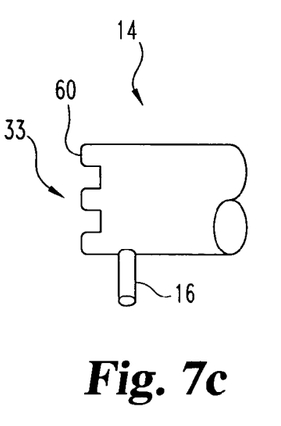
FIG. 7c illustrates an end portion of a containment housing having an end wall with ridges or fins for use in association with an expandable containment device.

Referring to FIGS. 7a-7c, shown therein are other embodiments of the housing 14 illustrated and described about which include various anchor elements or surface features 33 extending from the end wall to facilitate gripping or secure engagement with the adjacent vertebral body or bone to inhibit movement of the containment device 10. As illustrated in FIG. 7a, the anchor elements or surface features 33 comprise one or more teeth or spikes 56. As illustrated in FIG. 7b, the anchor elements or surface features 33 comprise one or more projections or knurlings 56. As illustrated in FIG. 7c, the anchor elements or surface features 33 comprise one or more ridges or fins 60. It should be understood that other types or configurations of anchor elements or features are also contemplated as falling within the scope of the present invention. Although not specifically illustrated, it should be understood that either or both of the upper and lower housings may be provided with anchor elements or surface features.

Figure 8:
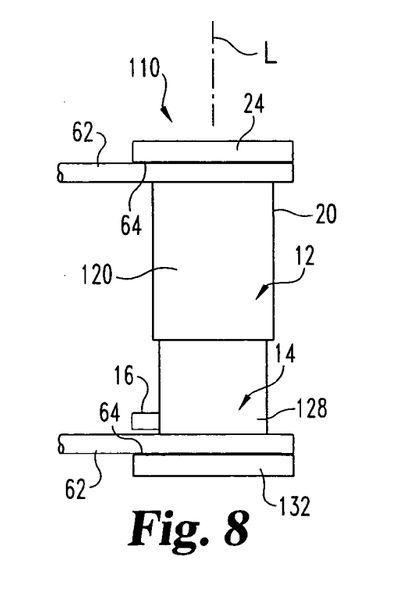
FIG. 8 illustrates an expandable containment device according to another form of the present invention for use in conjunction with an external distractor instrument.

Referring to FIG. 8, shown therein is another embodiment of a containment device 110 extending generally along a longitudinal axis L and including an upper housing 112, a lower housing 114 and an input port 116. The containment device 110 is configured identical to the containment device 10 illustrated and described above, with the exception that at least a portion of each of the ends walls 124 and 132 of the upper and lower housings 112, 114, respectively, extend beyond the axial side walls 120, 128 so as to define a pair of opposing shoulders or abutments 64. An external distractor instrument is provided including a pair of distractor arms 62. The distractor arms 62 are engaged against the opposing shoulders or abutments 64 to expand or spread the upper and lower housings 112, 114 apart to expand the containment device 10. Various types of distractor instruments are contemplated for use in association with the present invention, including scissor-type distractors, gear-driven distractors, and any other type of distractor instrument know to those of skill in the art.

In another embodiment of the present invention, two distractor instruments may be used to expand the containment device, with one arm of the first distractor engaged with a portion of the upper housing and the other arm engaged against the vertebral body or bone positioned adjacent the lower housing, and with one arm of the second distractor engaged with a portion of the lower housing and the other arm engaged against the vertebral body or bone positioned adjacent the upper housing. The two distractor instruments may then be used to pull the upper and lower housings apart to expand the containment device. In other embodiments, a distractor instrument may be used to spread the vertebrae apart while the containment device expands independently via injection of flowable material M into the containment device.

Figure 9:
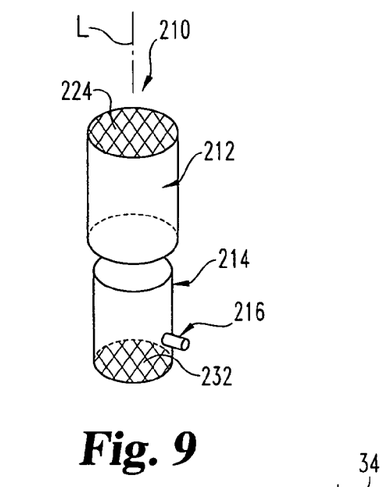
FIG. 9 illustrates an expandable containment device according to another form of the present invention.
Figure 10A:
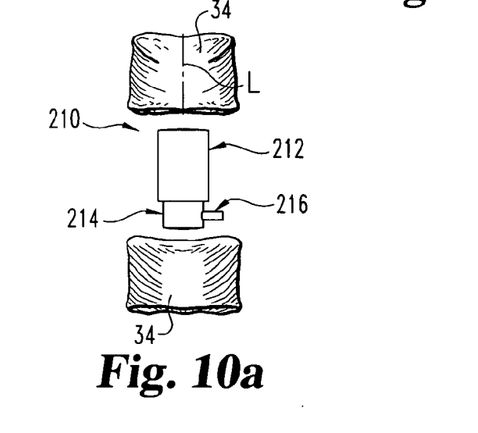
FIG. 10a illustrates the expandable containment device of FIG. 9, as positioned between adjacent vertebrae in a contracted state.
Figure 10B:
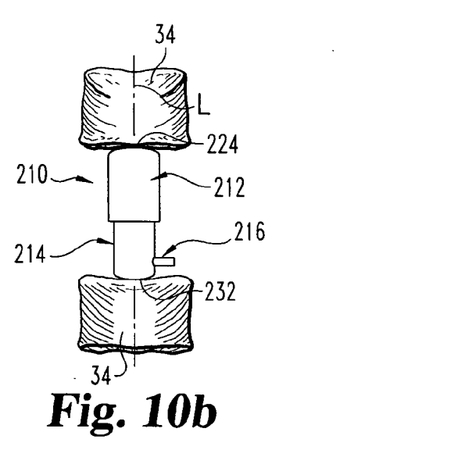
FIG. 10b illustrates the expandable containment device of FIG. 9, as positioned between adjacent vertebrae in an expanded state.

Referring to FIGS. 9 and 10a-10b, shown therein is another embodiment of a containment device 210 extending generally along a longitudinal axis L and including an upper housing 212, a lower housing 214 and an input port 216. The containment device 210 is configured identical to the containment device 10 illustrated and described above, with the exception that at least a portion of each of the ends walls 224 and 232 of the upper and lower housings 212, 214, respectively, are formed of a flexible material so as to allow the end walls 224, 232 to more closely conform to the shape of the adjacent vertebrae 34 or bone to which they are engaged. As shown in FIG. 10b, as the containment device 210 is expanded via injection or delivery of the flowable material into the interior region, internal fluid pressure within the containment device 10 exerts pressure against the flexible end walls 224, 232 to cause the walls 224, 232 to outwardly deform or bubble out to more closely conform to the shape of the adjacent vertebrae 34 or bone. The flexible end walls 224, 232 may be formed integral with the remainder of the housing or may be formed separately and attached or connected to the remainder of the housing via various techniques know to those of skill in the art. The flexible material may comprise latex, silicone, a polymer based material such as polyethylene, polyester, a fabric material, or any other flexible material know to those of skill in the art. Additionally, the flexible material may be somewhat porous in nature to allow a certain amount of the flowable material M to seep through the end walls 224, 232 to provide additional engagement with the adjacent vertebral body or bone.

Figure 11A:
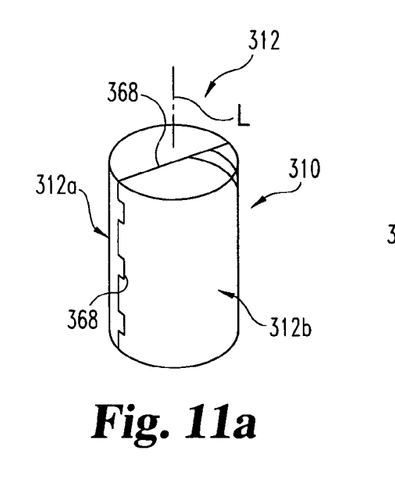
FIG. 11a illustrates an expandable containment device according to another form of the present invention.
Figure 11B:
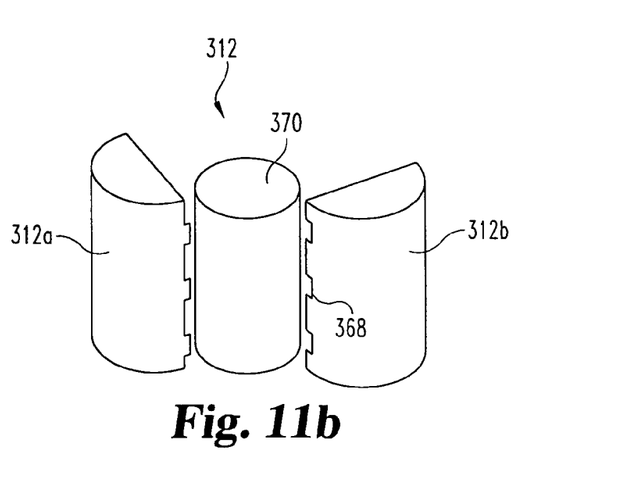
FIG. 11b illustrates the expandable containment device of FIG. 11a in a disassembled state.

Referring to FIGS. 11a and 11b, shown therein is another embodiment of a containment device 310 extending generally along a longitudinal axis L and including a housing 312 comprising a first lateral housing segment 312a and a second lateral housing segment 312b. In the illustrated embodiment, the housing segments 312a, 312b are generally symmetrical relative to the longitudinal axis L. However, other non-symmetrical configurations are also contemplated. The housing segments 312a, 312b are capable of being attached or connected to one another to form an integral housing 312. In the illustrated embodiment, the housing segments 312a, 312b are attached to one another via a tongue and groove arrangement 68 to provide the housing 312 with a clam-shell configuration. However, other attachment or connection techniques are also contemplated as falling within the scope of the present invention, the likes of which would be apparent to one skill in the art. Once the flowable material M has been injected into the interior region of the containment device and has set or cured to a hardened state, the housing segments 312a, 312b may be separated apart, thereby leaving a support column or strut 370 extending between the adjacent vertebrae or bone segments. Although not specifically illustrated, it should be understood that either or both of the upper and lower housings may be divided into lateral housing segments which are selectively separable from one another.

The components of the expandable containment devices illustrated and described above may be formed of various types of biocompatible materials. In one embodiment, the containment device is formed of a plastic or polymer material. In another embodiment, the upper and lower housings are formed of a thin plastic or polymeric material to allow excess material to be trimmed from the upper housing and/or the lower housing. In other embodiments, the containment devices are formed of hardened or cured bone cement or paste such as, for example, PMMA. In a specific embodiment, the containment devices are formed of the same flowable material that is injected into the hollow interior of the device. In still other embodiments, the components of the containment devices may be formed of a bioabsorbable or bioresorbable material such that the containment device is absorbed or resorbed into the body over a period of time so as to leave behind only the column or strut of hardened material. The containment devices may also be formed of other biocompatible materials including, but not limited to, non-reinforced polymers, carbon-reinforced polymer composites, PEEK and PEEK composites, shape-memory alloys, titanium, titanium alloys, cobalt chrome alloys, stainless steel, ceramics, or any other biocompatible material that would occur to one of skill in the art. Additionally, radiographic markers may be located at various locations on the containment devices to provide the ability to monitor and determine radiographically or fluoroscopically the location of the upper and lower housings relative to one another and/or relative to the adjacent vertebral bodies.

Although the various embodiments of the expandable containment devices illustrated and described above have been disclosed as having a substantially cylindrical configuration, it should be understood that other shapes and configurations are also contemplated as falling within the scope of the present invention. For example, it is also contemplated that, in some applications, it may be desirable to provide the containment devices with a substantially D-shaped configuration such that the anterior portion of the device has an exterior convexly curved surface corresponding to the anterior of the vertebral body, while the posterior portion of the device is substantially flat or concave to allow the device to be positioned closer to the spinal canal without protruding into the spinal canal. In other embodiments, the containment devices may be provided with a rectangular or square configuration, an oval or elliptical configuration, a polygonal configuration, or any other configuration that would occur to one of skill in the art. Additionally, the size and shape of the containment devices may be selected to substantially match the implantation site, and may be configured to correspond to the shape or contour of the adjacent vertebrae or bone structures.

While the present invention has been described with respect to insertion of the expandable containment devices within an intervertebral space between two vertebrae following removal of at least a portion of an intervening vertebra and the adjacent discs, it is also contemplated that the containment devices may be sized to span multiple vertebral levels to replace multiple vertebral bodies. Additionally, the containment devices may find application in other orthopedic areas outside of the spine.

Additionally, access to the surgical site may be accomplished via any surgical approach that will allow adequate visualization and/or manipulation of the bone structures. For example, surgical approaches include, but are not limited to, any one or combination of anterior, antero-lateral, posterior, postero-lateral, transforaminal, and/or far lateral approaches. Additionally, insertion of the containment device can occur through a single pathway or through multiple pathways, or through multiple pathways to multiple levels of the spinal column. Minimally invasive techniques using various types of instruments and devices are also contemplated.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable containment device for use in containing a flowable material, comprising:
    an expandable housing extending along a longitudinal axis and defining an interior region said expandable housing including a first housing portion movably engaged with a second housing portion to allow expansion of said housing generally along the longitudinal axis to provide said housing with an axial dimension extending between adjacent bone structures; and
    an input port in fluid communication with said interior region and configured to deliver a flowable material into said interior region of said expandable housing; and
    wherein said first and second housing portions are each configured as non-load bearing structures formed of a non-metallic material; and
    wherein said flowable material sets to a hardened state to provide a load-bearing support column extending between the adjacent bone structures.

2. The expandable containment device of claim 1, wherein said first and second housing portions are forced apart in response to delivery of the flowable material into the interior region of the expandable housing.

3. The expandable containment device of claim 1, wherein the flowable material comprises bone cement or paste.

4. The expandable containment device of claim 1, wherein at least one of said first and second housing portions includes a pre-scored section extending peripherally about said at least one of said first and second housing portions to allow for selective removal of an end portion of said at least one of said first and second housing portions.

5. The expandable containment device of claim 1, wherein each of said first and second housing portions includes an end wall defining at least one aperture in communication with said interior region of said housing to allow delivery of a portion of the flowable material into contact with a corresponding one of the bone structures.

6. The expandable containment device of claim 1, wherein each of said first and second housing portions includes an end wall having a flexible portion that outwardly deforms in response to delivery of the flowable material into said interior region of said housing to substantially conform said end wall to a surface of a corresponding one of the bone structures.

7. The expandable containment device of claim 1, wherein at least one of said first and second housing portions comprises at least two lateral housing segments configured to be selectively separated from one another and removed from the flowable material when set to a hardened state.

8. The expandable containment device of claim 1, wherein said flowable material comprises a semi-rigid material selected from the group consisting of silicone or urethane.

9. The expandable containment device of claim 1, wherein said non-metallic material is selected from the group consisting of a polymer material and a plastic material.

10. The expandable containment device of claim 1, wherein said interior region of said housing has a volume bound by inner surfaces of said first and second housing portions, said volume is entirely filled with said flowable material in direct contact with said inner surfaces of said first and second housing portions.

11. The expandable containment device of claim 1, wherein said first and second housing portions are each configured as non-load bearing structures formed of a non-metallic material; and wherein said flowable material sets to a hardened state to provide a load-bearing support column extending between the adjacent bone structures.

12. The expandable containment device of claim 1, wherein said non-metallic material comprises a flexible material to provide said first and second housing portions with one or more flexible portions.

13. The expandable containment device of claim 12, wherein said one or more flexible portions comprises an end wall that outwardly deforms in response to delivery of said flowable material into said interior region of said housing to substantially conform said end wall to a surface of a corresponding one of the bone structures.

14. The expandable containment device of claim 1, wherein said non-metallic flexible material is selected from the group consisting of a polymer material and a plastic material.

\* \* \* \* \*